United States Patent [19]

Stouder, Jr.

[11] Patent Number: 5,211,633
[45] Date of Patent: May 18, 1993

[54] SELECTABLE SEAL CANNULA

[76] Inventor: Albert E. Stouder, Jr., Doctors Park, R.R. 4, Tipton, Ind. 46072

[21] Appl. No.: 903,370

[22] Filed: Jun. 24, 1992

[51] Int. Cl.$^5$ ............................................. A61M 5/178
[52] U.S. Cl. ..................................... 604/167; 604/256
[58] Field of Search ......................... 604/256, 265-268, 604/237, 167

[56] References Cited

U.S. PATENT DOCUMENTS

| | | |
|---|---|---|
| 4,000,739 | 1/1977 | Stevens . |
| 4,177,814 | 12/1979 | Knepshield et al. . |
| 4,655,752 | 4/1987 | Honkanen et al. ................... 604/256 |
| 4,895,346 | 1/1990 | Steigerwald . |
| 4,895,565 | 1/1990 | Hillstead ............................... 604/167 |
| 4,909,798 | 3/1990 | Fleischhacker et al. ............. 604/256 |
| 5,020,543 | 6/1991 | Rothenberg et al. ............ 604/167 X |
| 5,041,097 | 8/1991 | Johnson . |
| 5,092,857 | 3/1992 | Fleischhacker . |

Primary Examiner—John D. Yasko
Attorney, Agent, or Firm—Woodard, Emhardt, Naughton, Moriarty & McNett

[57] ABSTRACT

A surgical cannula with selectable seals which assure a fluid-tight fit around medical devices of a variety of sizes. The cannula includes a tubular member insertable into a medical patient and having a side wall defining a lumen through which a medical device may be inserted. The cannula also includes a housing mounted to a proximal end of the tubular member wherein the housing has a passage allowing insertion of a medical device therethrough and into the lumen. A movable member is mounted to the housing and is selectively movable between a first position and a second position across the passage. When the movable member is in its first position the passage accommodates insertion of a first medical device having a first outer cross-sectional dimension. A first valve body is mounted in the movable member and has a first opening therein corresponding in size to the outer cross-sectional dimension of a smaller second medical device, wherein the first opening is smaller than the passage. When the movable member is in its second position the first valve body provides a fluid tight seal around the second medical device.

12 Claims, 6 Drawing Sheets

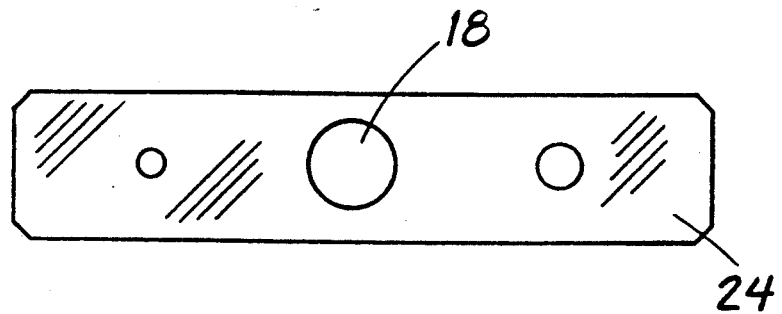
FIG. 7
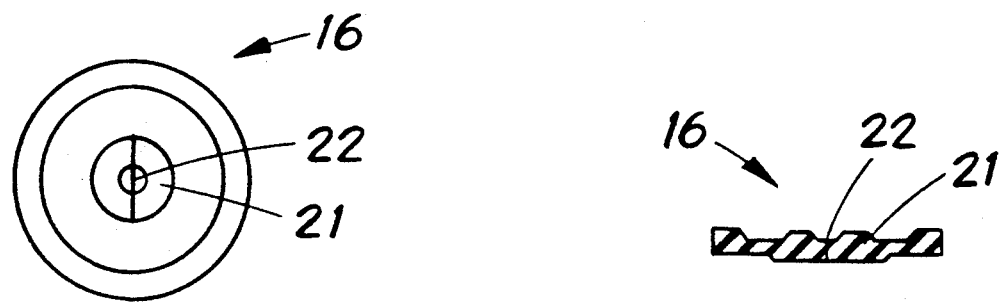
FIG. 8    FIG. 9
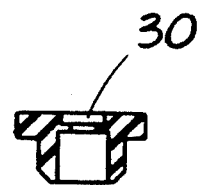
FIG. 10

SELECTABLE SEAL CANNULA

BACKGROUND OF THE INVENTION

This invention relates generally to surgical cannulas, and more particularly to a laparoscopic cannula which provides a fluid-tight seal around laparoscopic instruments of various outer diameters.

In medical procedures such as laparoscopy the patient's abdomen is distended to allow access to and visibility of the abdominal cavity. In order to distend the abdominal cavity a gas is injected into the cavity at a pressure of about 12 torr. The gas insuflates the abdominal cavity, supporting the abdominal walls up and away from the internal organs. Without this maintained pressure the abdominal wall collapses and all visibility through the laparoscopic camera is lost.

While the abdomen is distended with gas, cannulas through which medical instruments can be inserted traverse the abdominal wall. Valves are typically included in these cannulas to prevent air from leaking from the pressurized cavity when the laparoscopic cannula is in use. The competence of these valves is of great importance because even a small leak in the cannula may cause a decrease in insufflation pressure and the attendant collapse of the abdominal wall.

A variety of laparoscopic instruments are used with such cannulas. For example, laparoscopic forceps, clamps, scalpels, etc., are all known. These laparoscopic instruments are typically round in cross section, and have outer diameters ranging from about 2 mm to about 1 cm. In many laparoscopic procedures it is necessary to remove a larger laparoscopic instrument and to replace it with a smaller instrument during the course of the procedure. It is not practical to replace the cannula at such times.

Laparoscopic cannulas are available with lumen diameters of 5 mm, 1 cm, etc., with the larger sizes being preferred for laparoscopic procedures in which larger-diameter laparoscopic instruments may be required. The valve employed in the cannula may be any valve which seals around medical instruments, such as a slit valve, etc. However, all single-valve systems are known to leak when the smallest laparoscopic instruments are used in large-lumened cannulas.

Presently, the insertion of small instruments into the 1 cm or larger cannulas requires a reducing gasket to prevent significant air loss. In the larger cannulas of the prior art, such as the TROCAN TM 5 mm Disposable Surgical Trocar and Cannula No. 004536-901, the reducing gasket is a plastic cap which is inserted over the outer opening of the cannula to reduce the effective size of the opening. It can be appreciated that changing the reducing gasket is a time-consuming inconvenience to the medical team since the gasket must pass from the nurse to the doctor before being applied to the cannula. The time and effort required to change prior art gaskets is an undesirable aspect of such devices.

A need therefore exists for a universal cannula which may rapidly be adapted to accept laparoscopic instruments of varying sizes and to provide a fluid-tight seal around such instruments. The present invention addresses this need. Furthermore, the present invention has applicability in other surgical procedures such as cardiological procedures involving inserting guide wires, catheters and other medical devices into a medical patient's blood vessels or other body cavities.

SUMMARY OF THE INVENTION

Briefly describing the present invention, there is provided a surgical cannula with selectable seals which assure a fluid-tight fit around medical devices of a variety of sizes. The cannula includes a tubular member insertable into a medical patient and having a side wall defining a lumen through which a medical device may be inserted. The cannula also includes a housing mounted to the proximal end of the tubular member wherein the housing has a passage allowing insertion of a medical device therethrough and into the lumen. A movable member is mounted to the housing and is selectively movable between a first position and a second position across the passage. When the movable member is in its first position the passage accommodates insertion of a first medical device having a first outer cross-sectional dimension. A first valve body is mounted in the movable member and has a first opening therein corresponding in size to the outer cross-sectional dimension of a smaller second medical device, wherein the first opening is smaller than the passage. When the movable member is in its second position the first valve body provides a fluid-tight seal around the second medical device.

The present invention also provides a method of using a surgical cannula having a movable member with selectable seals to assure a fluid-tight interface when the cannula is used in combination with various sized medical devices.

One object of the present invention is to provide a cannula which provides a fluid-tight seal when used with medical instruments having a wide range of outer diameters.

Another object is to provide an improved surgical cannula.

A further object of the present invention is to provide a method of using a selectable seal cannula.

Related objects and advantages of the present invention will be apparent from the following description.

DESCRIPTION OF THE DRAWINGS

FIG. 7 is a top plan view of the movable member tray cover of the present invention.

FIG. 8 is a top plan view of a valve fixed in the housing of the present invention.

FIG. 9 is a cross-sectional view of the valve of FIG. 8.

FIG. 10 is a cross-sectional view of a gasket used in the movable member of the present invention.

DESCRIPTION OF THE PREFERRED EMBODIMENT

Figure 1:
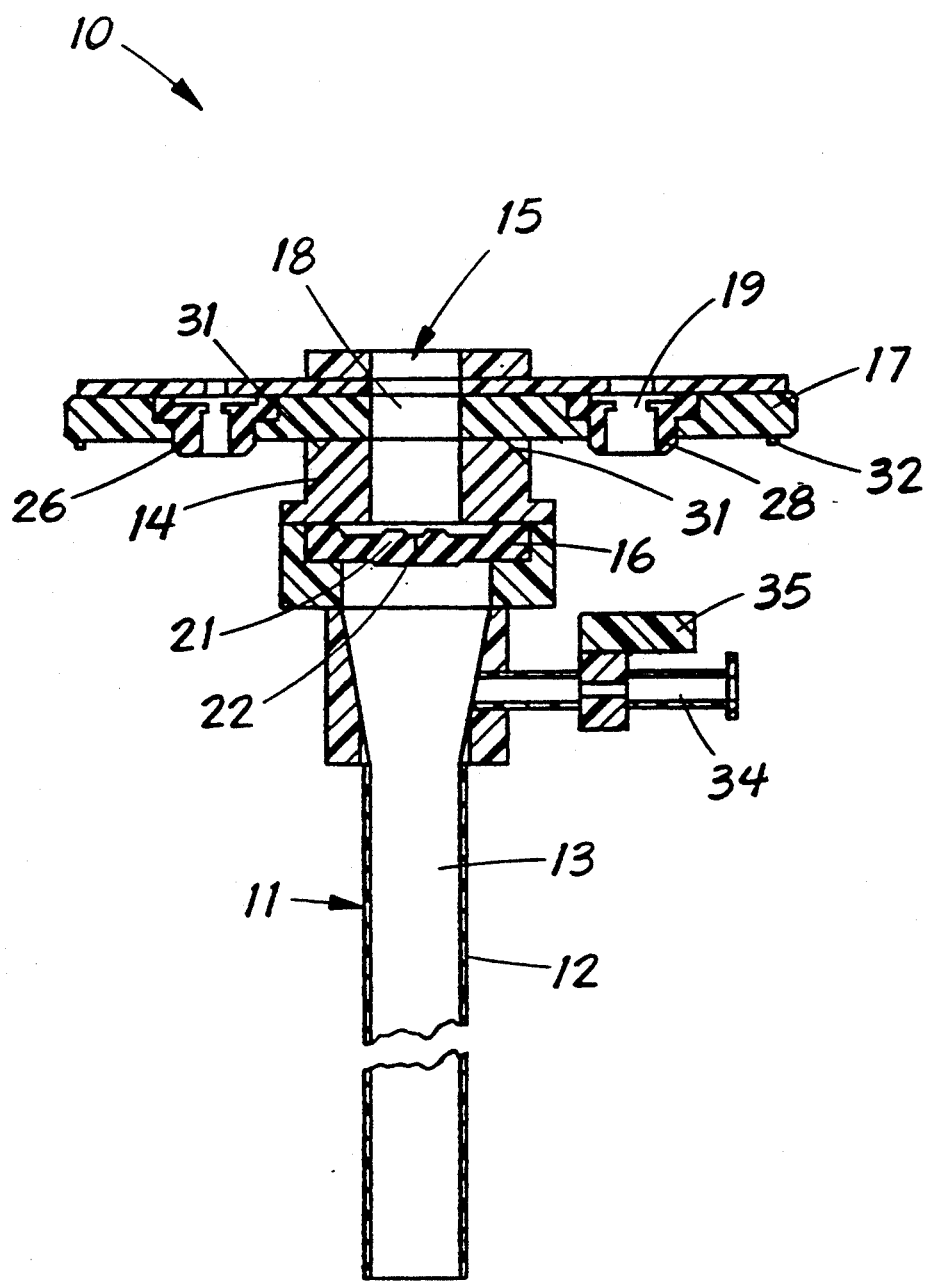
FIG. 1 is a side cross-sectional view of the cannula of the present invention according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and method, and such further applications of the principles of the invention as illustrated herein being contemplated as would normally occur to one skilled in the art to which the invention relates.

Figure 11:
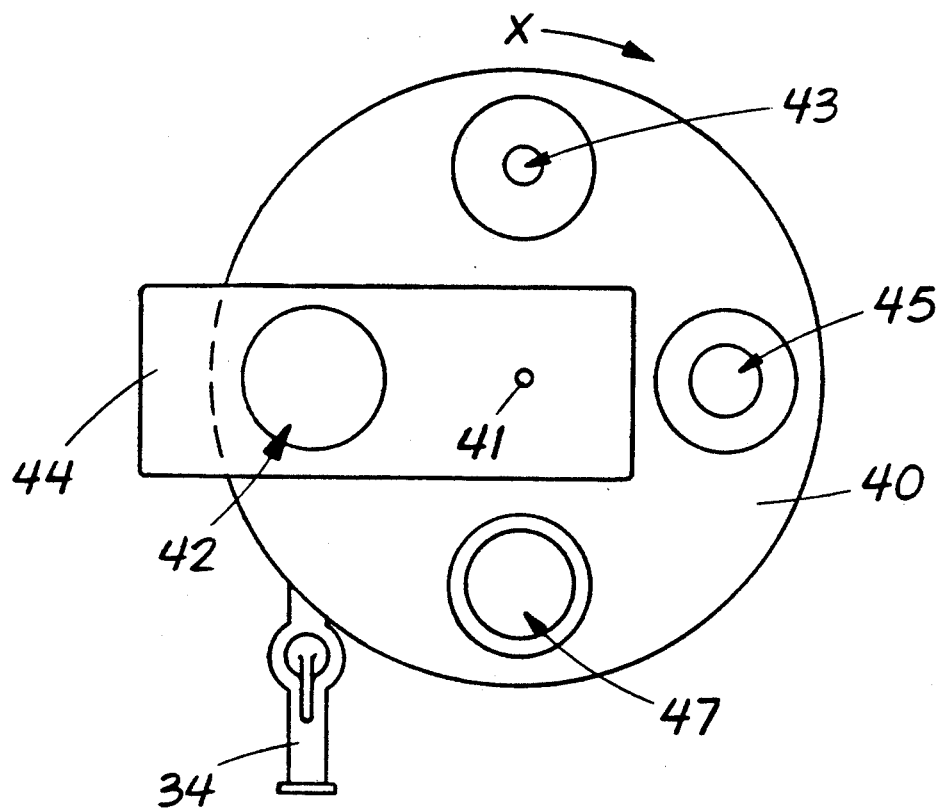
FIG. 11 is a top plan view of an alternative embodiment of the present invention wherein the movable member is rotatably movable with respect to said housing.

Referring now to the drawings, FIGS. 1 through 10 illustrate the universal cannula according to one preferred embodiment, while FIG. 11 illustrates an alternative embodiment of the device.

Universal cannula 10 includes a tubular member 11 which traverses the abdominal wall and serves as a conduit through which laparoscopic or other medical instruments can be passed. Tubular member 11 may be made of stainless steel or otherwise and includes a side wall 12 defining a lumen 13. The lumen is preferably one centimeter in diameter, although larger or smaller lumen sizes may be used.

A housing 14 is mounted to the proximal end of tubular member 11. Housing 14 includes a passageway 15 aligned with lumen 13 to allow medical instruments to be passed through the cannula. Housing 14 also preferably includes a valve 16 fixed in the passageway to provide an airtight seal around large-diameter laparoscopic instruments when such instruments are used. Fixed valve 16 also prevents air from leaking through the cannula when no laparoscopic instrument is being used.

Concerning specifically fixed valve 16, the design is of the slit valve type. The valve has an offset superior protrusion 21 close to the center 22 of the valve. This helps decrease air leakage when using 5 mm-diameter instruments. When these instruments are passed through the valve the silastic will be pushed downward and the protrusions will effectively make the valve opening smaller. This action snugs the silastic around the 5 mm instrument and decreases the amount of air that escapes through the valve. Note that when using smaller instruments this valve alone may not provide adequate sealing.

Accordingly, additional valves may be provided on movable member 17 mounted to the housing. Movable member 17 is selectively movable between a first position and a second position across passageway 15. When movable member 17 is in its first position (FIGS. 1 and 2), larger-sized medical devices such as instrument Ml having a diameter D1 may be inserted through the cannula as shown in FIG. 2. When movable member 17 is in its second position (FIG. 3), a gasketed aperture 19 with an opening smaller than the passageway is aligned with the lumen so that smaller-sized laparoscopic instrument may be inserted without fluid leaks.

Figure 5:
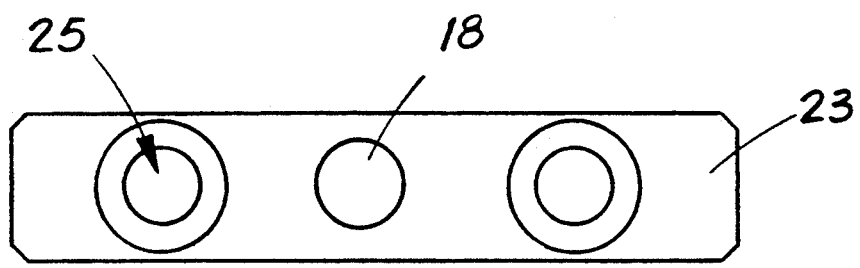
FIG. 5 is a top plan view of one embodiment of the movable member tray of the present invention.
Figure 6:
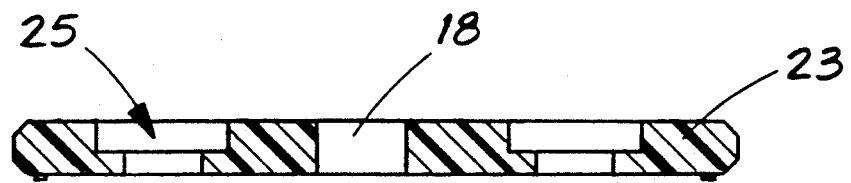
FIG. 6 is a side cross-sectional view of the movable member tray of FIG. 5.

Movable member 17 preferably includes a tray 23, a tray cover 24, non-valved aperture 18 and one or more valves held in respective apertures, such as aperture 25, in the tray (see FIGS. 5 and 6). Each valve preferably comprises a gasket 26 or 28 with an aperture 27 or 29, respectively, which is smaller than the passageway to prevent air loss when small-sized medical instruments are used. Thus, even if fixed valve 16 leaks the smaller valves in the gaskets remain competent, thus maintaining integrity of the system.

The gaskets 26 and 28 used in movable member 17 are preferably silastic gaskets which provide a fluid-tight seal around laparoscopic instruments inserted through the cannula. Preferred gaskets include a constricted portion 30 (see FIG. 10) in the upper portion of the gasket. The constricted portion is preferably slightly smaller than the instruments used so that the gasket forms a seal around the instrument. In addition, the constricted portion assists in minimizing the contact with the laparoscopic instrument so that the frictional force of moving the instrument in and out will not be enough to dislodge the gasket from its sealed position. It is to be understood that any number of valve/gasket configurations may be used, including multiple slits, punctures, multilayered gaskets and the like.

Housing 14 also preferably includes bevels 31 at the edges of the surface across which movable member 17 slides. These bevels serve to assist in pushing the silastic gasket up into the tray when the bottom of the gasket slides through the housing to the passageway. By sliding the tray in either direction the bottom of the gasket will hit the beveled housing. Since the silastic is somewhat compressible, it will bulge into the hole in its center, as well as elevate slightly, as the movable member and gasket slide through the housing toward the passageway. When the gasket is positioned in the passageway the gasket will seat in that opening and by expansion to its usual size will form a seal. A stop, such as stop member 32, may be provided at the ends of the movable member to prevent it from accidentally falling out of the housing.

Although in one embodiment the movable member includes one gasketed aperture and one non-gasketed aperture, in alternative embodiments two or more gasketed apertures are provided so that a wider range of laparoscopic or other medical instruments may be used. In preferred embodiments movable member 17 includes three apertures. The center, non-valved aperture 18 is typically a hole which is provided so that large-sized laparoscopic instruments may be inserted into the cannula passageway. For example, aperture 18 may have a diameter D5 (see FIG. 4) of one centimeter which is large enough to accommodate most larger-sized instruments. When the non-valved aperture of movable member 17 is aligned with the passageway, fixed valve 16 prevents air loss and the collapse of the abdominal cavity. The other apertures include gaskets as described above which remain competent against fluid leaks when smaller-diameter instruments are used. For example, first valve gasket 26 may include a gasket to provide a 3 mm diameter D3 aperture 27, while second valve gasket 28 may include a gasket to provide a 5 mm diameter D4 aperture 29. The gasket openings are smaller than passageway 15 (i.e., D3 and D4 are both smaller than D5) and preferably correspond in size to the outer cross sectional dimensions of a small-diameter laparoscopic instruments.

The valve gaskets of the present invention preferably all have a common outer dimension, whereas the inner opening of the gasket varies in size according to its intended use. It is to be appreciated that such valve gaskets may be quickly and easily interchanged, and that any size of inner valve opening may be supplied. Further, the apertures 25 holding the valve gaskets are preferably countersunk to prevent the gasket or valve body used in the aperture from slipping through. While the inner shape and size of the apertures in the valves/gaskets are typically referred to in terms of "diameter", it is to be understood that this term encompasses non-circular shapes of various sizes corresponding to medical instrument to be used.

Figure 2:
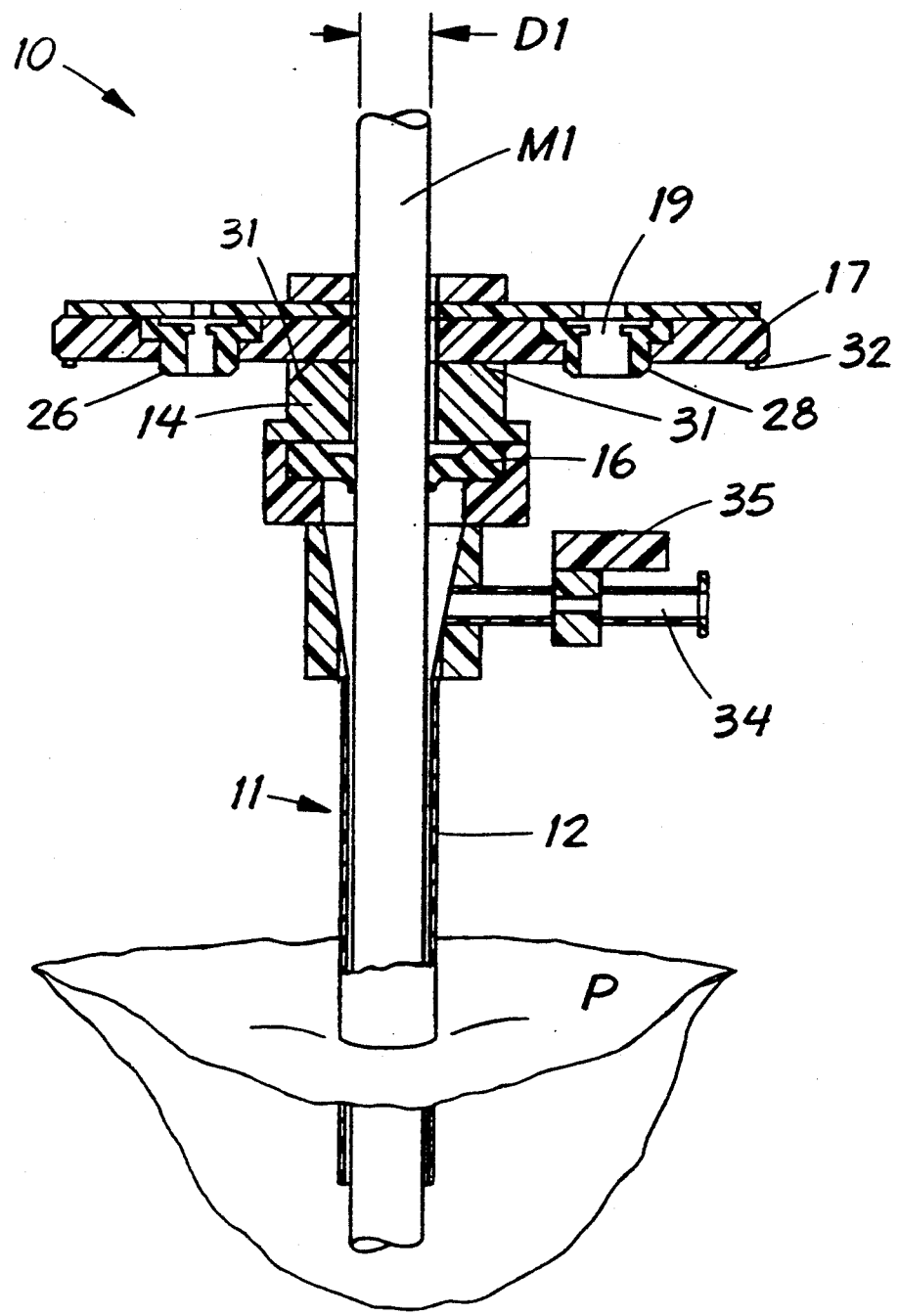
FIG. 2 is a side cross-sectional view of the cannula of FIG. 1 inserted in a medical patient and with a large-sized medical device inserted through the cannula.
Figure 3:
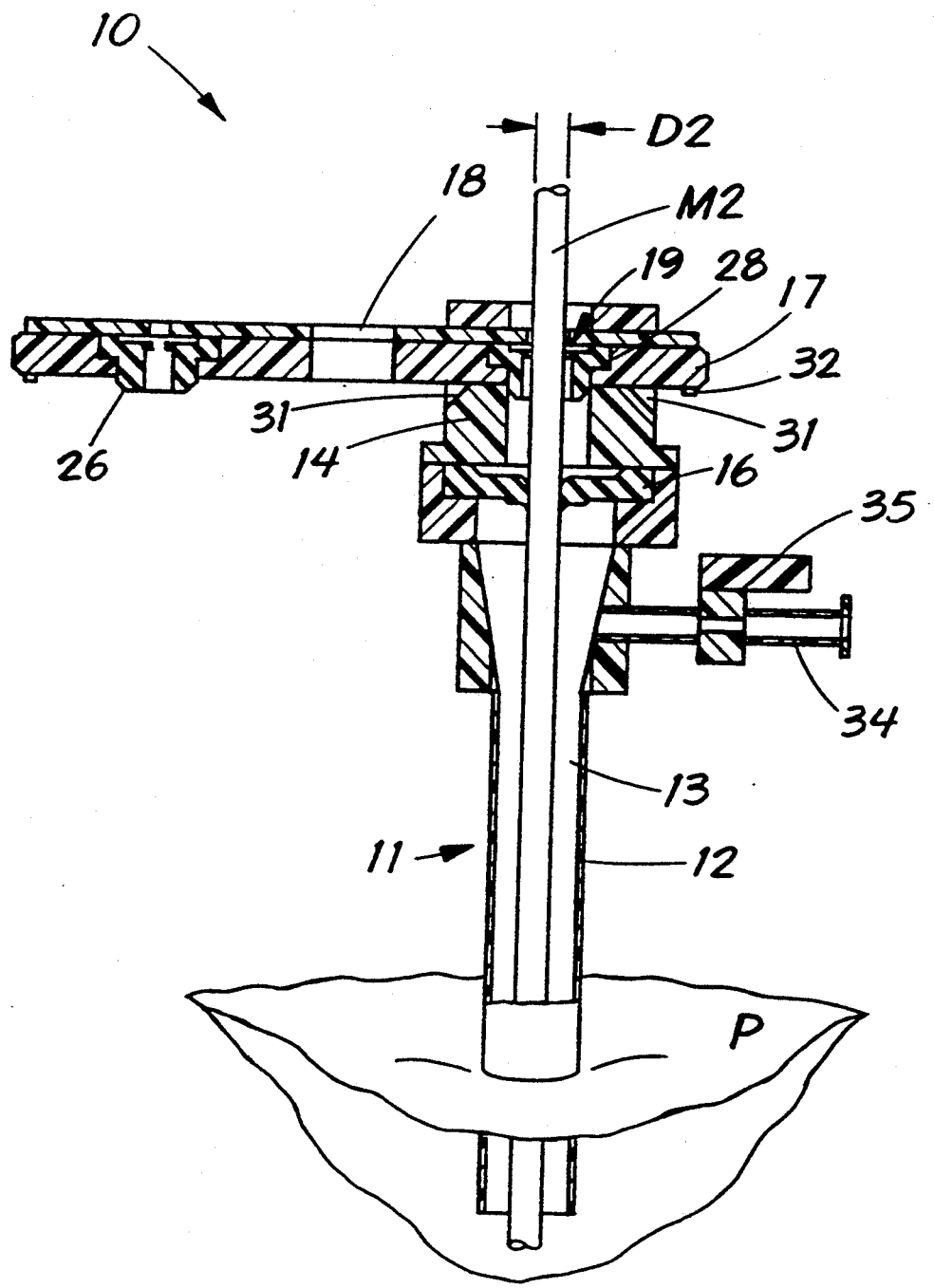
FIG. 3 is a side cross-sectional view of the cannula of FIG. 2 with a smaller-sized medical device inserted through the cannula.
Figure 4:
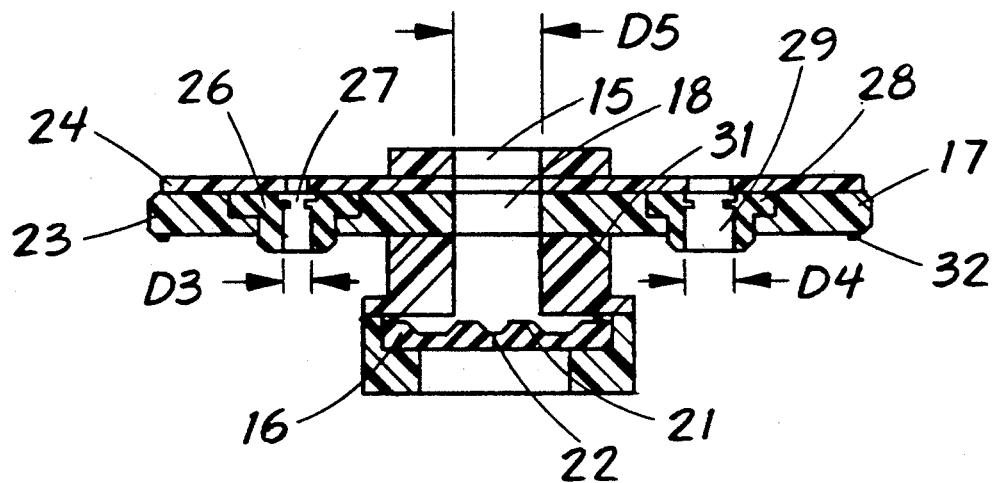
FIG. 4 is a side cross-sectional view of the housing and movable member of the device of FIG. 1.

A side port 34 may also be included in the cannula (see FIGS. 1-3). Side port 34 allows fluids to be supplied or withdrawn through the cannula. Side port 34 may further include a valve 35 to control the flow of fluids through the port. Port 34 is preferably located fluidally between valve 16 and tubular member 11, allowing fluid control through the port even when a medical instrument is removed and valve 16 is closed.

A method of using the cannula of the present invention includes the following steps. First, tubular member 11 is inserted and secured in a medical patient P. A first medical device M1 with a first outer diameter D1 is inserted into the lumen and used as is known to those skilled in the art. After using the first medical device, that device is removed. The movable member of the present invention, including a first valve body, is thereafter positioned so that the first valve body is aligned with the lumen. A second medical device M2 with a second outer diameter D2 is inserted through the first valve body and into the lumen. The opening of the first valve body is smaller than the lumen, so that the first valve body provides a fluid-tight seal around said second medical device.

It is to be appreciated that the movable member need not be a rectangular tray radially slidable across the passageway of the cannula. For example, movable member 40 may be circular, like a wheel or disk, so that the smaller-sized valves are rotatably movable with respect to the housing. As can be seen in FIG. 11, in this embodiment movable member 40 rotates about a pivot 41 somewhat offset from the passageway 42 of a cannula. When movable member 40 is rotatably moved in path X with respect to the housing 44, the apertures 43, 45, 47 and 49 positioned over the cannula passageway can be rapidly and selectively changed. Other embodiments which selectively position a valve member in the passageway of a cannula may also be employed such as a transversely slidable arcuate-shaped tray movable in an arcuate path.

A number of variations are contemplated to be within the scope of applicant's invention and may be included to adapt the device to a particular use without changing the basic features. For example, movable member 17 may optionally be positioned beneath valve 16 instead of above valve 16 as illustrated in the Figures. Therefore, while the invention has been described in detail in the foregoing description of the preferred embodiment, this description is to be considered illustrative and not restrictive in character. It is to be understood that only the preferred embodiments have been shown and described, and that all changes and modifications within the spirit of the invention are desired to be protected.

I claim:

1. A surgical cannula, comprising:
   a tubular member insertable into a medical patient and having a side wall defining a lumen through which a medical device is to be inserted;
   a housing mounted to a proximal end of said tubular member, wherein said housing has a passage allowing insertion of a medical device therethrough and into said lumen;
   a movable member mounted to said housing and selectively movable between a first position, a second position and a third position across said passage, wherein when said movable member is in said first position said passage accommodates insertion of a first medical device having a first outer cross-sectional dimension;
   a first valve body mounted in said movable member and having a first opening therein corresponding in size to an outer cross-sectional dimension of a smaller second medical device, wherein said first opening is smaller than said passage, and wherein when said movable member is in said second position said first valve body provides a fluid tight seal around said second medical device; and
   a second valve body mounted in said movable member and having a second opening therein corresponding in size to an outer cross-sectional dimension of a smaller third medical device, wherein said second opening is smaller than said first opening, and wherein when said movable member is in said third position said second valve body provides a fluid tight seal around said third medical device.

2. The cannula of claim 1 and further including a separate elastomeric fixed valve body mounted in said housing and providing a fluid tight seal across said passage when no medical devices are inserted through said passage.

3. The cannula of claim 2 and further comprising a side port into said housing, wherein said side port is mounted to said housing between said tubular member and said fixed valve body, and wherein said side port has an on/off valve therein to allow selective fluid flow control through said side port.

4. The cannula of claim 3 wherein said passage comprises a circle at least ten millimeters in diameter, wherein said first opening is a circle about five millimeters in diameter, and wherein said second opening is a circle about three millimeters in diameter.

5. The cannula of claim 4 wherein said movable member has a gasketless hole therein to accommodate insertion of the first medical device when said movable member in said first position.

6. The cannula of claim 5 wherein said movable member is transversely slidably movable with respect to the passage of said housing.

7. The cannula of claim 1 and further comprising a side port into said housing, wherein said side port has an on/off valve therein to allow selective fluid flow control through said side port.

8. The cannula of claim 1 wherein said movable member has a gasketless hole therein to accommodate insertion of the first medical device when said movable member in said first position.

9. The cannula of claim 1 wherein said movable member is transversely slidably movable with respect to the passage of said housing.

10. The cannula of claim 1 wherein said movable member is rotatably movable with respect to said housing.

11. The cannula of claim 5 wherein said movable member is rotatably movable with respect to said housing.

12. The cannula of claim 1 wherein said passage comprises a circle at least ten millimeters in diameter, wherein said first opening is a circle about five millimeters in diameter, and wherein said second opening is a circle about three millimeters in diameter.

* * * * *